(12) United States Patent
Verbiscar

(10) Patent No.: US 6,858,232 B2
(45) Date of Patent: Feb. 22, 2005

(54) TOPICAL TRANSDERMAL TREATMENTS

(76) Inventor: Anthony J. Verbiscar, 160 E. Montecito Ave., Sierra Madre, CA (US) 91024

(*) Notice: Subject to any disclaimer, the term of this patent is extended or adjusted under 35 U.S.C. 154(b) by 0 days.

(21) Appl. No.: 09/795,589

(22) Filed: Feb. 28, 2001

(65) Prior Publication Data

US 2001/0012840 A1 Aug. 9, 2001

Related U.S. Application Data

(63) Continuation-in-part of application No. 09/320,700, filed on May 26, 1999.
(60) Provisional application No. 60/087,406, filed on Jun. 1, 1998.

(51) Int. Cl.[7] .............................................. A61K 35/78
(52) U.S. Cl. ..................................................... 424/725
(58) Field of Search ......................................... 424/725

(56) References Cited

U.S. PATENT DOCUMENTS 5,750,563 A * 5/1998 Honda
5,760,096 A * 6/1998 Thornfeldt et al.
5,945,409 A * 8/1999 Crandall
5,968,530 A * 10/1999 Arquette

FOREIGN PATENT DOCUMENTS

EP 267617 * 5/1988
SU 111903 * 5/1958

OTHER PUBLICATIONS

Yukawa et al., Yakuzaigaku, 1989, 49(3), 254–62.*

* cited by examiner

*Primary Examiner*—Michael Meller

(57) ABSTRACT

Jojoba alcohol, a mixture of long chain monounsaturated alcohols, is an oily liquid at moderate ambient temperatures. It is readily absorbed by human skin where it relieves irritation and inhibits the formation of lesions caused by viruses. The inhibitory action is applicable to enveloped viruses such as herpes simplex, which express as sores at dermal surfaces in humans. When applied topically to an incipent herpes episode, it will quickly penetrate the epidermis to the subdermal vascular cells and suppress viral replication which leads to inflammation and the formation of blisters on the face, genital and other skin and mucosal areas. Compositions of certain low molecular weight organic acids in jojoba alcohol enhance antiviral activity. Jojoba alcohol is a carrier and transdermal delivery system for these and other pharmacologically active agents for the relief of pain and treatment of other conditions which occur at or under the surface of the skin. Topically applied jojoba alcohol is non-toxic and safe for animals and humans.

35 Claims, No Drawings

TOPICAL TRANSDERMAL TREATMENTS

RELATED U.S. APPLICATION

This application is a continuation in part of U.S. Ser. No. 09/320,700, filed May 26, 1999, now abandoned. Which claims priority from Provisional Application No., filed Which claims the benefit of Provisional Application No. 60/,087,406, filed Jun. 1, 1998.

FIELD OF INVENTION

This invention relates to methods for the use of liquid mixtures of long chain monounsaturated alcohols such as jojoba alcohol and their compositions for the topical transdermal treatment of subdermal infections such as by herpes simplex viruses, and the local dermal delivery of pharmacological agents for the treatment of various diseases and other conditions, such as pain.

BACKGROUND OF INVENTION

A large percentage of the world population are infected with herpes viruses. Three of the most common herpes viruses are herpes simplex virus-1 (HSV-1) which is the cause of facial and ocular sores, herpes simplex virus-2 (HSV-2) which has a predilection for genital areas, and herpes simplex virus-3 (HSV-3), also named herpes zoster and varicella zoster, which causes chicken pox and later shingles. Human herpes virus-8 is associated with the skin cancer Kaposi sarcoma. These herpes episodes are each susceptable to topical treatments because the viruses replicate in subdermal cells during a recurrence leading to an eruption into a lesion. Inhibition of viral fusion with or entry into a host cell is a treatment method disclosed here versus herpes viruses using a mixture of long chain monounsaturated alcohols represented by jojoba alcohol as the inhibitor. Examples of transdermal delivery of drugs are also described. More than 275 unique chemical compounds and compositions have been reported as skin penetration enhancers for transdermal drug delivery (Osborne and Henke, www.pharmtech.com/technical/osborne/osborne/htm).

Once an individual is infected, herpes viruses become latent principally in nerve cells, and can reactivate to cause recurrences of the original symptoms. When a herpes virus infected individual undergoes stress from exhaustion, strong sunlight, wind, certain foods and medications, menses or microbial infection, the virus migrates to vascular cells under the epidermis where it begins to replicate. For HSV-1 and HSV-2 the initial itchiness, tingling or pain is referred to as the prodromal stage signaling that the virus is active under the skin. Prodromal can occur from an hour to several days before an outbreak of lesions. At the erythema or inflammation stage, the immune system has begun to fight the virus. After this irritating redness stage, vesicles form and eventually erupt into lesions on the skin and mucosal surfaces. HSV-1 and HSV-2 are morphologically indistinguishable, the main difference being where the sores appear on the skin, and there is some interchange in recurrence sites between these two viruses. Herpes migration to the brain or spinal cord leads to encephalitis and meningitis, which are life-threatening conditions.

There are several treatment options for herpes infections but no cures. Several of the nucleoside analog drugs can be effective if taken prophylactically on a daily basis. They are less effective if administered at the time of the recurrence, either orally or topically. The nucleoside drugs inhibit viral replication by penetrating into the cell and interfering with nucleic acid production. They are not virucidal, and depend on a functional immune system to deactivate any virus present. A number of commercial "cold sore" preparations are available which treat symptoms, but are generally ineffective in preventing the formation of lesions. They contain principally anesthetic, antibacterial, emolient and wound healing compounds which can reduce pain, prevent microbial infection and help dry up the blister. Topical treatments of herpes simplex virus infections have been reviewed (Hamuy and Berman, Europ. J. Dermatol., 8:310–319, 1998; Evans and Tyring, Dermatol Clinic, 16: 409–419, 1998; Syed et al., Clin Drug Invest., 16: 187–191, 1998).

Alcohols with chain lengths of 16 to 20 carbon atoms and 1 to 4 double bonds inhibited herpes simplex and another lipid enveloped viral bacteriophage in cell cultures (Sands et al., Antimicrob. Agents Chemother., 15: 67–73, 1979). These unsaturated alcohols were more potent in vitro than saturated alcohols with shorter chain lengths (Snipes et al., Antimicrob. Agents Chemother., 11: 98–104, 1977). A patent (Rivici et al., U.S. Pat. No. 4,513,008, 1985) describes the inhibition of enveloped viruses such as herpes with linear polyunsaturated acids, aldehydes or primary alcohols with chain lengths of 20 to 24 carbons and 5 to 7 double bonds. These reports were followed by the investigations and development of n-docosanol as a topical treatment for herpes infections.

n-Docosanol, also named 1-docosanol and behenyl alcohol, is a straight chain 22 carbon saturated alcohol, which occurs in the bark, flowers and fruit of the tree *Pygeum africanum*. n-Docosanol is reported to have broad activity in cell cultures against lipid enveloped viruses such as herpes (Katz et al., Proc. Nat. Acad. Sci., 88:10825–10829, 1991; Katz et al., Ann. N.Y.Acad. Sci., 724: 472–488, 1994; Pope et al., J. Lipid Res., 37: 2167–2178, 1996; Pope et al., Antiviral Res., 40:85–94, 1998), and also the human inmmunodeficiency virus HIV (Marcelletti et al., AIDS Research and Human Retroviruses, 12: 71–74, 1996). These studies demonstrated that the antiviral activity of n-docosanol includes inhibition of the process of viral entry into the cell, while being mediated by intracellular metabolic biotransformation of the drug. A series of patents on the composition of mixtures of n-docosanol in formulations that render it useful for topical application supports these published reports (Katz, U.S. Pat. No. 4,874,794, 1989; Katz, U.S. Pat. No. 5,071,879, 1991; Katz, U.S. Pat. No. 5,166,219, 1992; Katz, U.S. Pat. No. 5,194,451, 1993; Katz, U.S. Pat. No. 5,534,554, 1996). n-Docosanol is not virucidal deactivating viruses directly, but it interferes with viral replication, and depends on a functional immune system to destroy herpes viruses. n-Docosanol is a crystalline waxy solid insoluble in water which needs to be formulated with a non-ionic surfactant and carrier to facilitate dermal penetration and interaction at the target cell level. This limitation was also noted where several other long chain compounds with 18 plus linear carbons including amides, alkanes, acids and alcohols needed to be formulated with a surfactant and carrier to facilitate penetration of the epidermis (Katz et al., U.S. Pat. No. 5,534,554, 1996; Katz et al., PCT WO98/11887, 1998; Katz et al., U.S. Pat. No. 5,952,392, 1999). The latter patents claim a composition of n-docosanol or other long chain compounds with a surfactant and a pharmaceutically acceptable diluent or carrier as the active viral replication inhibitor, rather than the pure individual compounds. The solid long chain alcohols and other compounds are not be expected to penetrate skin layers alone without a carrier. In a study using 10% n-docosanol suspended in an aqueous system containing a non-ionic surfactant and a carrier, mean healing time of lesions in humans infected with herpes labialis (HSV-1) was shortened (Habbema et al., Acta Derm. Venereol., 76: 479–481, 1996). A 12% n-docosanol cream was tested as a possible transmision prophylactic of simian immunodeffi-ciency virus (SIV) in rhesus macque monkeys (Miller et al., Antiviral Res., 26: A277, 1995). Intravaginal application before exposure prevented transmission in five of the six monkeys tested. n-Docosanol and other saturated alcohols with chain lengths of 20 to 26 carbons reportedly promote corneal healing due to eye injury (Muller, U.S. Pat. No. 5,214,071, 1993; Muller, U.S. Pat. No. 5,296,514, 1994).

Jojoba oil, obtained from the seeds of the desert shrub *Simmonsia chinensis*, is a mixture of mono esters composed principally of both long chain monounsaturated alcohols and carboxylic acids (Miwa and Spencer, Proc. Second Int. Conf. on Jojoba and Uses, Ensenada, Baja Calif., Mexico, 229–243, 1976). Jojoba oil has been available commercially for more than twenty years, and several million pounds are used in cosmetic formulations annually. A significant characteristic of jojoba oil is its ability to be absorbed quickly by the ski This ready absorption has been related to the single carbon—carbon double bond occurring in the interior of both the alcohol and carboxylic acid parts of the mono ester molecules. Extensive testing and use of jojoba oil has established that it is completely safe when applied to human skin, or administered orally to mice, rats, marmots and rabbits (Taguchi and Kunimoto, Cosmetics and Toiletries, 92: 53–61, 1977; Clark and Yermanos, Biochem. Biophys. Res. Commun., 102: 1409, 1981; Hamm, J. Food Sci., 49: 417–428, 1984; Verschuren and Nugteren, Food Chem. Toxicol., 27: 45–48, 1989). Humans who have ingested jojoba seeds, which are 50% oil, have not been harmed, although some nausea occurred when as much as 200 grams were eaten. In mice, jojoba oil has functioned as an intestinal lubricant (Verbiscar et al., J.Agric. Food Chem., 28: 571–578, 1980). It is estimated that about 20% of jojoba oil is split by hydrolytic enzymes in the gastrointestinal system, thus producing jojoba alcohol in situ. After dermal absorption, jojoba oil is at least partially metabolized to jojoba alcohol. Jojoba oil is a generally recognized as safe product for cosmetic uses throughout the world.

Jojoba alcohol has been prepared from jojoba oil by hydrogenolysis with sodium and alcohol (Molaison et al, J. Amer. Oil Chem. Soc., 36: 379–382, 1959). An improved hydrogenolysis of jojoba oil has been reported (Verbiscar, U.S. divisional patent application, Feb. 12, 2001).

In these hydrogenolysis reactions, the carboxylic acid part of the ester is converted to its corresponding alcohol, in contrast to chemical hydrolysis where the fatty acids remain intact and must be separated from the alcohols in the mixture. Hydrogenolysis doubles the amount of jojoba alcohol that can be obtained from jojoba oil. One jojoba alcohol product prepared by hydrogenolysis was reportedly a mixture of octadec-9-enol, eiocos-11-enol, docos-13-enol and tetracos-15-enol (Taguchi, Proc. Sixth Int. Conf. Jojoba and Its Uses, eds. Wisniak and Zabicki, Ben-Gurian Univ. Negev, Beer-Shiva, Israel, p 371–391, 1984). The actual alcohol composition will vary according to the source of jojoba oil used in the hydrogenolysis. The relative amounts of individual alcohol components in jojoba alcohol depends on the ester composition of jojoba oil , a product obtained from seeds harvested in the Southwestern United States, Mexico, Israel and South America (Miwa, Spencer and Plattner, Proc. Second Int. Conf. Jojoba and Uses, Ensenada, Baja Calif., Mexico, 187–197, 1976). Plant variety, pollination, soil, climate and other cultural conditions will cause the chemical composition of jojoba oil, and thus jojoba alcohol, to vary. There is no single combination of alcohols, nor a percent range, that defines jojoba alcohol. Mixtures of monounsaturated alcohols can also be prepared from other sources, such as by the hydrogenolysis of sperm whale oil, a monoester similar to jojoba oil, or even from some plant triglycerides. In addition, a mixture of the alcohol components can be prepared by combining each individual alcohol in any specific amount. A formulated mixture of individual long chain alcohols will act like jojoba alcohol. Jojoba alcohol can actually be comprised of a number of individual principally long chain monounsaturated alcohols depending on the source of the seeds from which jojoba oil is derived. Jojoba alcohol is used here as a generic term representing mixtures of these alcohols which will remain liquefied at ambient temperatures above about three degrees centigrade.

Pure long straight chain monounsaturated alcohols are waxy liquids or low melting solids, but when in a mixture as in jojoba alcohol exist as a colorless odorless oil at normal ambient temperatures. A characteristic of jojoba alcohol is that it is readily absorbed by human skin and does not require a carrier or surfactant to facilitate transdermal penetration. Jojoba alcohol is reported as a lipstick component along with a large number and variety of carboxylic acids, esters and alcohols with diverse structures and functions (Sato, Lipocolor Composition, U.S. Pat. No. 5,700,453, 1997). It is mentioned as an excipient in a formula with kojic acid (Honda, U.S. Pat. No. 5,750,563, 1998). The use of jojoba alcohol or any mixture of long chain monounsaturated alcohols as a skin penetration enhancer is new, unique and not previously known among such compositions (Osborne and Henke, ibid). Koey Perfumery Co., Tokyo, a company that introduced jojoba oil commercially as a cosmetic ingredient, also investigated the the safety of jojoba alcohol for cosmetic uses (Taguchi, 1984 ibid). The following mouse, rabbit, marmot and human tests were made for jojoba alcohol confirming that this product is very safe for topical application. Mutagenicity tests were also negative.

Acute Oral Toxicity In Mice Sixty inbred mice, 30 each male and female, separated into three groups, were fed jojoba alcohol with a stomach tube in a single dose. The first group received 32 ml/kg (27 g/kg), the second 40 ml/kg (34 g/kg), and the third group received 50 ml/kg (42.5g/kg). There were no deaths in any group after 7 days, so the oral LD50 value is above 50 ml/kg. The average weight dropped on day 1 but increased normally thereafter. Jojoba alcohol probably acts as an intestinal lubricant similar to jojoba oil, causing a weight change in the first 24 hours due to elimination of nutrients along with the jojoba alcohol in feces. There were no observed anatomical changes. Jojoba alcohol was not orally toxic to mice at these dose levels.

Ocular and Dermal Rabbit Tests Jojoba alcohol was dissolved in jojoba oil at three concentration levels of 50%, 25% and 12.5% on a w/w basis. The rabbits, three per dose level group, were administered 0.05 ml (1 drop) of these solutions in the right eye. The left eye was not treated. Eye irritation was very low with no effects on the cornea and iris, and mild conjunctivitis clearing up within 24–48 hours. In another test, ten male albino rabbits were treated with cloth strip patches on the skin with each of these three samples. Patches were removed from 5 rabbits after 15 days and from the remaining 5 rabbits after 30 days. Visual and pathological examination of the treated skin areas indicated that irritation was quite low and comparable among the three samples.

Dermal and Subcutaneous Marmot Tests Jojoba alcohol was dissolved in high purity jojoba oil at a 10% concentration. Albino marmots, 10 males and 10 females, were treated with this sample in a patch test. There was no sign of any irritation after 24 and 48 hours. In another test, the 10% solution of jojoba alcohol in jojoba oil was injected subcutaneously into 10 each male and female marmots. After 24 and 48 hours there was no evidence of irritation at the injection site. After one week the jojoba alcohol solution was spread on a cloth patch, and the patch was placed on the injection site. After two weeks a jojoba alcohol solution sample patch was placed on a challenge site away from the site of injection. No sensitization was observed at any of the sites.

Dermal Patch Human Tests A test was carried out on 40 humans with healthy skin. Two samples including 100% jojoba alcohol and 10% jojoba alcohol in jojoba oil were prepared on cloth strip patches. The patches were applied on the upper part of the back of 20 subjects for each sample. Results were observed after 30 minutes and after 24 hours. No evidence of irritation of any kind was observed in 39 of the subjects, and only one of the subjects on the 10% formula showed a possible reaction. A second test was carried out on another 40 subjects with contact dermatitis using pure jojoba alcohol on cloth strips patches. Only one of the test subjects showed a doubtful reaction in the first 30 minutes, and there were no positives after 24 hours. Jojoba alcohol is dermally non-toxic.

SUMMARY OF THE INVENTION

Jojoba alcohol is an oily liquid that is readily absorbed by human skin, leaving no residue nor odor. When applied to an incipient herpes simplex virus recurrence, it quickly penetrates the epidermal layer to the subdermal cells where viral replication leading to symptomatic disease would otherwise occur. Jojoba alcohol appears to function by inhibiting lipid enveloped viruses from fusing with and entering cells. Irritation is relieved and viral replication is delayed, while the host immune system is alerted to destroy the free virus units. When treated early in the prodrome or even the erythema inflammation stages, herpes blisters do not form or at least are inhibited in persons with functional immune systems. This inhibitory action is applicable to enveloped viruses which express as lesions at epidermal surfaces. Herpes simplex viruses which cause recurrent facial sores (HSV-1) and genital sores (HSV-2), shingles (HSV-3) and Kaposi sarcoma (HHV-8) are treatment targets. Jojoba alcohol also functions as a transdermal carrier for pharmacologically active agents that act at or under dermal surfaces.

DETAILED DESCRIPTION OF THE INVENTION

In tests with mice and guinea pigs it was established that jojoba alcohol is not a virucide nor a microbiocide, which destroy viruses directly. Jojoba alcohol is a virustat which delays viral replication by inhibiting cellular penetration. The nucleoside analog drugs such as acyclovir and penciclovir which are used for oral and topical treatments of viral infections are also virustats acting by interferring with nucleic acid production inside the infected cell. For virustats to be effective, it is necessary for a functional immune system to respond and destroy the virus. Accordingly, it is important to treat herpes recurrences as soon as possible after the virus becomes active, in order to minimize the viral load to be eliminated by the immune system.

Jojoba alcohol is most effective versus herpes recurrences in the prodrome stage, just as the skin is becoming irritated and inflammed, when the immune system begins its response to the localized infection. Early applications every several hours works best, eliminating itchiness and irritation caused by lysis of infected cells. Jojoba alcohol spread on an irritated area of the skin penetrates quickly and is active without the need for a carrier. Compared to small alcohol molecules such as ethanol and isopropyl alcohol, which evaporate or are carried away into the circulation, jojoba alcohol will remain active under the general area of skin application for an extended period of time. Its insolubility in water and the absence of a surfactant limit its absorption into the circulation and removal from the active subdermal site, thereby enhancing activity.

In a preferred embodiment, alpha d-tocopherol (vitamin E) is added to jojoba alcohol to improve stability against oxidation of the double bonds. Tocopherols are the natural antioxidents which occur in jojoba seeds and in pressed or extracted jojoba oils. In a further embodiment, salicylic acid is added as an antiviral, antiseptic and keratolytic agent. This broadens the efficacy of jojoba alcohol and improves its healing power. Other low molecular weight organic acids such as lactic acid, glycolic acid, pyruvic acid, benzoic acid and acetylsalicylic acid will also enhance antiviral efficacy (Poli et al., Food Chem., 4:251–258, 1979; Brown-Skrobot et al., U.S. Pat. No. 4,975,217, 1990; Primache et al., Microbiologica, 21: 397–401, 1998) when present in jojoba alcohol. Additional food grade low molecular weight di- and tri-carboxylic organic acids which in cell cultures have shown activity against herpes and other viruses include malic acid, fumaric acid, succinic acid tartaric acid and citric acid, but they are formulated with jojoba alcohol into a lower alcohol to improve solubility.

The structure of the major components of this generic jojoba alcohol mixture and examples of the principal individual monounsaturated alcohols composing jojoba alcohol follows:

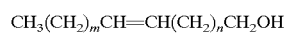

$$CH_3(CH_2)_m CH{=}CH(CH_2)_n CH_2OH$$

|  | m | n |
|---|---|---|
| Hexadec-7-enol | 7 | 5 |
| Octadec-7-enol | 9 | 5 |
| Octadec-9-enol | 7 | 7 |
| Eicos-11-enol | 7 | 9 |
| Docos-13-enol | 7 | 11 |
| Tetracos-15-enol | 7 | 13 | where the double bond can exist in cis and trans forms and m and n can vary from 5 to 13 carbons.

Mouse and Guinea Pig Studies The HSV-2 infected mouse system used here was designed to discover products which have potential to be used in a single dose prophylactic mode against infection. This is principally the domain of virucides, or microbiocides. Viracol is a virustatic and was only expected to delay infection in the mice, which it did as in Example 1. The guinea pig system of Example 2 extends antiinfection tests to first episodes, which are far more severe than recurrences. A principal reason for this is that the newly infected host's immune defense system is not yet programmed to fight this particular virus. Jojoba alcohol merely delays viral entry into the cell where the virus must penetrate in order to replicate. This delay mechanism relies upon an effective immune system to destroy the virus. Jojoba alcohol can only be used to inhibit recurrences, and must be applied several times every few hours after the first feeling of irritation signalling an incipient recurrence. Treatment of an infected guinea pig every twelve hours as in Example 2 is inadequate for a virustatic which delays viral replication. The application protocol was too infrequent in an animal with a high dose of inoculum, and an immune defense system not yet alerted to the virus. Tests in humans against recurrences of herpes episodes are the best way to evaluate efficacy.

Human Studies Preliminary tests of jojoba alcohol against herpes labialis (HSV-1) in human subjects were done with pure distilled product with no additives. In one test a 65 year old female subject who normally experiences about two cold sores per year was exposed to strong sunlight for an extended period of time. One day after this exposure the subject began to experience itching and mild inflammation in her upper lip and nasal (perioral) area. One drop of jojoba alcohol was applied and spread around the irritated area, and this was repeated four hours later. Early symptoms disap peared quickly and no lesions formed. This result was typical of several preliminary tests of jojoba alcohol versus herpes simplex virus-1 episodes in human subjects.

Example 3 describes the protocol used to test jojoba alcohol preparations versus HSV-1 induced facial sores and HSV-2 induced genital sores. Results are in Table 1 and Table 2. In these Tables, jojoba alcohol is formulated with 0.5–1% alpha-d-tocopherol as an antioxidant, and named Viracol. The composition Viracol Plus contains 2% salicylic acid.

In Table 1, 15 subjects reported a total of 30 recurrences. In 14 (47%) of these episodes there were no sores at all. Another 8 episodes resulted in mild lesions. Several of the moderate to severe lesion recurrences were treated only after blister formation had already started. Several subjects with severe

TABLE I

Human Testing Of Viracol Versus Herpes Labialis (HSV-1)

| Subject | Gender | Age | Stage Start | Appl. Doses | Days | None | Mild | Mod. | Severe |
|---|---|---|---|---|---|---|---|---|---|
| 102 | M | 36 | pro | 9 | 1.5 | | | * | |
| 102 | | | pro | 3 | 1 | * | | | |
| 104 | M | 68 | ery | 8 | 3 | * | | | |
| 104 | | | ery | 3 | 1 | * | | | |
| 104 | | | pro | 3/d | 4 | * | | | |
| 107 | M | 40 | pro | 10/d | 7 | | | | * |
| 107 | | | pro | 10/d | 5 | | | | * |
| 107+ | | | pap | 10/d | 2 | | | * | |
| 115 | F | 50 | pro | 3 | 1 | * | | | |
| 115 | | | pro | 2 | 1 | * | | | |
| 115 | | | pro | 4 | 1 | * | | | |
| 132a | F | 50 | pap | 3/d | 6 | | | | * |
| 132 | | | pap | 10/d | 5 | | | * | |
| 132 | | | ery | 10/d | 7 | | | * | |
| 132+ | | | ery | 4/d | 4 | | * | | |
| 132+ | | | ery | 8 | 2.5 | | * | | |
| 133 | M | 52 | pap | 15 | 5 | | | * | |
| 138 | F | 32 | ery | 3 | 1 | | * | | |
| 140+ | F | 45 | ery | 70 | 17 | | | * | |
| 140+ | | | pro | 6 | 2 | * | | | |
| 140+ | | | ery | 10 | 3 | | * | | |
| 141[b] | F | — | pro | 1 | | * | | | |
| 142 | F | 19 | pro | 6 | 1 | * | | | |
| 145 | F | 33 | pap | — | 8 | | | * | |
| 151 | F | 67 | ery | 3 | 1 | * | | | |
| 151 | | | ery | 5 | 1.5 | * | | | |
| 153 | M | 49 | ery | 5 | 7 | | | * | |
| 153 | | | ery | 4 | 1 | | | * | |
| 174+[b] | F | — | pro | 6 | 2 | * | | | |
| 180+ | F | 45 | pap | 4 | | * | | | |
| Subjects | F = 10, M = 5 | | | | | 14 | 8 | 5 | 3 |

+ = Viracol Plus
pro = prodrome, ery = erythema, pap = papule
[a]Subject never without an outbreak of HSV-1 or HSV-2 in past year
[b]Also experiences genital HSV lesions

TABLE II

Human Testing Of Viracol Versus Herpes Genitalis (HSV-2)

| Subject | Gender | Age | Stage Start | Appl. Doses | Days | None | Mild | Mod. | Severe |
|---|---|---|---|---|---|---|---|---|---|
| 109 | M | 55 | ery | 3 | 4 | * | | | |
| 111 | M | 33 | pro | 10 | 3 | * | | | |
| 111 | | | pro | 4 | 2 | * | | | |
| 116 | M | 48 | pro | 3 | — | * | | | |
| 124 | F | 65 | pro | 12 | 4 | | * | | |
| 124 | | | pap | 12 | 6 | | | * | |
| 125 | F | 51 | ery | 4 | 2 | * | | | |
| 127 | M | 50 | ery | 2 | 2 | | | * | |
| 130 | M | 52 | pro | 5 | 2 | * | | | |
| 134 | F | 27 | pro | 10 | — | | | * | |
| 134 | | | ery | 5 | 3 | | | * | |
| 136 | M | 49 | pro | 2 | 4 | | | * | |
| 137 | F | 26 | pro | 3 | 2 | | | * | |
| 137 | | | pro | 2 | 1 | * | | | |

TABLE II-continued

Human Testing Of Viracol Versus Herpes Genitalis (HSV-2)

| Subject | Gender | Age | Stage Start | Appl. Doses | Days | Lesion Results None | Mild | Mod. | Severe |
|---|---|---|---|---|---|---|---|---|---|
| 139 | F | 36 | pap | 4/d | 8 | | | * | |
| 139 | | | ery | 4/d | 6 | | * | | |
| 141[b] | F | — | pro | 1 | 11 | | | | * |
| 143 | M | 40 | ery | 4 | 4 | * | | | |
| 143 | | | pro | 12 | — | * | | | |
| 148 | M | 44 | pap | 10 | 13 | | | | * |
| 148+ | | | ery | 10 | 4 | | * | | |
| 148+ | | | pro | 4 | 3 | | * | | |
| 148+[a] | | | pap | 3a | | | | * | |
| 165 | F | 36 | pro | 5 | | | * | | |
| 165 | | | ery | 5 | | | * | | |
| 173+ | F | 26 | pro | 6 | 2 | * | | | |
| 173+ | | | pro | 9 | 3 | * | | | |
| 173+ | | | pro | 3 | 2 | * | | | |
| 174+[b] | F | 59 | pap | 16 | 8 | | | * | |
| 174+ | | | ery | 3/d | 5 | * | | | |
| 174+[c] | | | pro | 3/d | 6 | | | | * |
| Subjects | F = 9, M = 8 | | | | | 15 | 9 | 4 | 3 |

+ = Viracol Plus
pro = prodrome, ery = erythema, pap = papule
[a]Ran out of Viracol before the episode ended
[b]Also experiences facial HSV lesions
[c]Induced by Staph infection episodes experienced improved results using Viracol Plus. At least one subject (102) experiences all of the symptoms of a cold sore recurrence at one time, with no warning period, but even he was successful in reducing blister formation. One female subject (132), diagnosed with Crohn's disease, has never been without a cold sore and chronic fatigue for more than one year due to a depressed immune system. After several trials with Viracol she was switched to Viracol Plus with improved results. A male subject (107) who also experienced frequent cold sores was also more successful with Viracol Plus. In Viracol Plus, jojoba alcohol acts as a virustatic, delaying viral entry into the cell, while acting as a transdermal delivery system for the solid salicylic acid which inhibits viral replication by a second mechanism related to an interaction with the glycoprotein in the envelope.

In Table 2, 17 subjects reported a total of 31 genital herpes recurrences. In 15 (48%) of these episodes, there was complete inhibition of lesion formation. Another 9 episodes resulted in mild lesions. Of the 7 episodes where moderate to severe lesions formed, treatment was initiated in 5 episodes at the papule or blister stage. One of these (141) treated her recurrence only once due to employment conditions. A female subject (174) who experienced both HSV-1 and HSV-2 recurrences had greater success with Viracol Plus.

A twelve year old girl experienced pain which after two days led to a few blisters at her waist.

Having had chicken pox as an infant, she was diagnosed as having a shingles episode induced by herpes simplex virus-3, also named herpes zoster and varicella zoster. Starting on the third day after initiation of pain, she was treated with Viracol six times per day and with oral famciclovir three times per day. The episode was terminated in seven days total. There was no pain and no additional blister formation after treatment was started with with Viracol. Shingles episodes can be severe and last for several weeks to a month or more.

Jojoba alcohol formulations can be used to treat both men and women with equal success against incipient dermal sores caused by herpes viruses. Results are best when treatment is started as early as possible at the prodrome or erythema stages. The treatments were well tolerated with no adverse effects. Viracol Plus containing salicylic acid improves overall antiviral activity and healing of any blisters that may form due to inadequate application of the jojoba alcohol product, or due to a depressed immune system. In this formulation, jojoba alcohol facilitates the transdermal penetration of salicylic acid, a crystalline solid, to the viral replication site.

Ibuprofen and ketoprofen are two nonsteroidal antiinflammatory drugs that are administered orally for management of pain. Some persons using these medications experience gastrointestinal side effects. Each of these drugs was formulated at a 2–5% level in jojoba alcohol. Both formulations successfully relieved pain when applied topically to skin surfaces over the site of the pain. In several cases, relief lasted for several hours following application of only several drops. There was no residue at the application site. The degree of relief varied at different pain sites with different individuals. In one woman with arthritis, a chronic pain in a thumb was relieved. A young boy was relieved of pain in a sprained tendon in the arch of his foot. Another woman used the ketoprofen product to relieve pain in her forearm muscles strained after working at a computer all day. Diclofenac is another oral pain relief drug that can be formulated with jojoba alcohol for transdermal local delivery against pain.

While the description above contains specifics, these should not be construed as limitations of the scope of the invention, but rather examples of preferred embodiments. Many more variations are possible for the use of jojoba alcohol and other mixtures of long chain monounsaturated alcohols as transdermal delivery agents. Other applications are numerous with several of these noted below, where jojoba alcohol represents any mixture of long chain monounsaturated alcohols.

Alpha hydroxy acids such as lactic acid and glycolic acid are used extensively in cosmetics to reduce wrinkles, spots and other signs of aging (Kurtzweil, Alpha Hydroxy Acids for Skin Care, FDA/CFAN report, U.S. Food and Drug Administration, Consumer Affairs, March-April, 1998). Jojoba alcohol will modulate penetration and safety aspects of these alpha hydroxy acids.

Capsaicin occurs in various edible peppers. It is used as a topical analgesic in gels and lotions to temporarily relieve minor aches and pains associated with arthritis, strains and sprains. Jojoba alcohol will facilitate transdermal penetration of capsaicin at the site of topical application.

Testosterone is a primary male hormone produced in the testes with effects on muscles, bones and sexual function. Testosterone replacement therapy for men with a deficiency, sometimes referred to as hypoganadism, is currently available in topical patches. A 1% testosterone solution in jojoba alcohol left no residue when applied to a subject's forearm, indicating that transdermal delivery was facilitated. This jojoba alcohol transdermal delivery technology can also be applied to corresponding estrogenic steroids such as estradiol for women.

Prostaglandin E1, also referred to as alprostadil, occurs in the male reproductive system acting as a peripheral vasodilator to support an erection. Several products containing this hormone are now available commercially, one for injection into the corpus cavernosum and one a urethral suppository. Prostaglandin E1 dissolves readily in jojoba alcohol, and facilitates transdermal delivery of this male hormone when applied topically to a penus. This safe and effective administration mode is an improvement over the current modes of administration of prostaglandin E1. Other delivery system enhancers for this hormone are being investigated (Eisenberg and Samour, U.S. Pat. No. 5,527,797, 1996).

Vitamin A (retinol) and/or vitamin D can be formulated with jojoba alcohol to treat psoriasis.

Pacitaxel (Taxol), its taxane analogs and other anticancer drugs can be formulated with jojoba alcohol as a penetration enhancer to treat skin cancers such as melanoma and Kaposi sarcoma.

Minoxidil is an antihypertensive drug currently in use as a hair growth stimulant. This active agent is formulated in propylene glycol as a carrier plus alcohol, presumably to facilitate penetration of the scalp. Both dropper and spray applications are available. Minoxidil can be formulated with jojoba alcohol as a transdermal penetration enhancer, which may also reduce itching and skin irritation side effects. Isopropyl alcohol or ethyl alcohol can be added to the formulation for application as a spray.

EXAMPLE 1

Prophylactic Test Versus Herpes Simplex Virus-2 in Mice

Thirty Swiss Webster female weanling mice with an average weight of 21 grams were divided into two groups of 15 controls and 15 treatment mice. Immediately before viral inoculation the controls were administered a placebo of phosphate buffer saline and the treatment mice were each administered 15 microliters of jojoba alcohol intravaginally. All 30 mice were then inoculated intravaginally with 10,000 pfu's of strain 186 herpes simplex virus-2 (HSV-2) and then maintained for 21 days. Results indicated that jojoba alcohol delayed the effects of HSV-2 infection in mice, namely death, but did not significantly prevent infection. On day 15 post inoculation, 80% of placebo mice had died compared to 40% of the treatment group. This effect could have resulted from limiting the initial viral replication in the genital tract, and thus decreasing the quantity of virus reaching latent storage sites in the ganglia. However, by day 21 only one treatment mouse survived and all placebo mice had died. This test clearly demonstrates that viracol is not virucidal and should not be used as a prophylactic to prevent transmission of HSV-2.

EXAMPLE 2

First Episode Test Versus Herpes Simplex Virus-2 In Guinea Pigs

Twenty four Hartley female guinea pigs weighing 300–350 grams were divided into two groups of 12 each, receiving jojoba alcohol and no treatment. Treatment animals received 0.05 ml (1 drop) of jojoba alcohol intravaginally, immediately followed in both groups by intravaginal inoculation of 75,000 pfu's of herpes simplex virus-2, a very high viral load which assures establishment of viral infection. Subsequent intravaginal/topical treatments with 0.05 mls of jojoba alcohol were applied 12 hours post viral inoculation, and continued twice daily every 12 hours for the following seven days. All animals were examined daily for evidence of primary episode herpetic disease, which began to appear on day 3 and continued for as long as day 10. Two treatment animals and one control remained asymptomatic. Jojoba alcohol did not significantly reduce the incidence or severity of this primary episode in guinea pigs, but there were no side effects due to intravaginal administration.

EXAMPLE 3

Human Studies Versus Herpes Simplex Viruses

A clinical study was undertaken using pure jojoba alcohol, a solution of 1% alpha-tocopherol in jojoba alcohol named Viracol, and a solution of 2% salicylic acid in Viracol named Viracol Plus. Male and female subjects of any age were enrolled who experienced at least 2 or 3 recurrences of herpes labialis (HSV-1) or herpes genitalis (HSV-2) per year. Exclusions included pregnant women, subjects on chronic antiviral chemotherapy, immunotherapy or alternative therapy, and hypersensitive individuals. Subjects were instructed to apply the jojoba alcohol products 3 to 5 times every 2 to 3 hours as soon as possible after initial irritation. They were provided with several reporting cards which included entries for the subject's code number, herpes virus identity, treatment date, number of applications, stage application started (prodrome, erythema, papule), lesions (none, mild, moderate, severe), total days of episode and side effects/comments. All subjects were volunteers, as were all herpes episodes meaning no recurrences were induced. Subjects were on an honor system to fill out the report cards after treating a recurrence, and mailing them back to the laboratory. Results are summarized in Table 1 and Table 2.

EXAMPLE 4

Nonsteroidal Antiinflammatory Agents In Jojoba Alcohol

Ibuprofen, alpha-methyl-4-(2-methylpropyl)benzeneacetic acid, is an orally active antiinflammatory agent. It was dissolved at a 5% level in jojoba alcohol containing 1% alpha-d-tocopherol as an antioxident. The oil was tested on several persons for relief of minor muscle and joint pains. Several drops of this preparation absorbs readily into human skin tissue with no visible residue, while relieving pain.

Ketoprofen, 3-benzoyl-alpha-methylbenzeneacetic acid, is an orally active antiinflammatory and analgesic agent. It was dissolved at a 3% level in jojoba alcohol containing 1% alpha-d-tocopherol as an antioxident. The oil was tested topically on several persons for relief of minor muscle and joint pains. Several drops of this preparation absorbs readily into human skin tissue with no visible residue, while relieving pain.

EXAMPLE 5

Low Molecular Weight Organic Acids in Jojoba Alcohol

Salicylic Acid is an antiviral, antiseptic and keratolytic agent. It was dissolved at a 2% level in jojoba alcohol. This beta-hydroxy acid enhances the efficacy of jojoba alcohol as an antiviral. It also improves healing power when applied at a papule stage of a herpes recurrence.

Acetylsalicylic Acid (aspirin) is an alalgesic, antipyretic and antiinflammatory agent that is also active against herpes simplex virus-3 (varicella zoster), the cause of chicken pox and shingles. Acetylsalicylic acid dissolves readily in jojoba alcohol.

Benzoic Acid is a food additive functioning as a preservative. Benzoic acid has germicidal activity and dissolves readily in jojoba alcohol.

Lactic Acid occurs naturally in yogurts and sour milk and is an acidulent used in foods. A 5% solution in jojoba alcohol absorbed readily into human skin with no irritation. Lactic acid is used in cosmetics, and has shown viral replication inhibition activity in cell cultures.

Glycolic Acid occurs in sugar cane juice. It dissolves readily in jojobal alcohol and is used in cosmetics. Glycolic acid has shown viral replication inhibition activity in cell cultures.

Pyruvic Acid is a natural component of muscle metabolism. Pyruvic acid dissolves readily in jojoba alcohol, and has shown viral replication inhibition activity in cell cultures

EXAMPLE 6

Di- and Tri-Carboxylic Organic Acids in Jojoba Alcohol Lotions

Malic Acid also known as hydroxysuccinic acid, occurs naturally in apples and is sometimes referred to as apple acid. It is used as a general purpose acidulent in food products. A 40 mg quantity dissolved readily in 3 ml of ethyl alcohol and 3 ml of jojoba alcohol resulting in a lotion containing 0.8% malic acid. This lotion applied to human skin absorbed readily and was non-irritating, leaving no residue. Malic acid has shown viral replication inhibition activity in cell cultures.

Citric Acid occurs in citrus and many other fruits, and is widely distributed in animal tissues. It is a sequestrant food additive and one of the active ingredients in Alka-Seltzer. A 35 mg quantity dissolved readily in 4 ml of isopropyl alcohol and 4 ml of jojoba alcohol resulting in a lotion containing 0.5% citric acid This lotion absorbed readily in human skin and was non-irritating, leaving no residue. Citric acid has shown viral replication inhibition activity in cell cultures.

Fumaric Acid is essential to animal tissue respiration. It is used as a substitute or partial replacement for tarric acid or citric acid in beverages. It can be formulated with jojoba alcohol and a lower alcohol such as ethyl alcohol and isopropyl alcohol as a lotion. Fumaric acid has shown viral replication inhibition in cell cultures.

Succinic Acid is used as a buffer and neutralizing agent in foods. It can be formulated with jojoba alcohol and a lower alcohol such as ethyl alcohol or isopropyl alcohol as a lotion. Succinic acid has shown viral replication inhibition activity in cell cultures.

What is claimed is:

1. A method for transdermal delivery of a phamiaceutically active agent to a subject in need thereof said method comprising:

a) preparing a formulation consisting essentially of said agent and a mixture of principally monounsaturated long chain alcohols having the structure:

$$CH_3(CH_2)_m CH=CH(CH_2)_n CH_2OH$$

wherein:
m and n are each independently 5 to 13,
said alcohols comprise 14 to 24 carbon atoms, and
the carbon-carbon double bonds are cia or trans, and b) applying the formulation produced in step (a) to the epidermis of said subject.

2. The method of claim 1 wherein the mixture of principally monounsaturated long chain alcohols is produced from jojoba oil.

3. The method of claim 1 wherein the mixture of principally monounsaturated long chain alcohols is produced from sperm whale oil.

4. The method of claim 1 wherein the mixture of principally monounsaturated long chain alcohols has a freezing point above three degrees centigrade.

5. A method for the topical treatment of a subject having a herpes virus infection, said method comprising:

a) preparing a formulation consisting essentially of a mixture of principally monounsaturated long chain alcohols effective for the topical treatment of herpes virus infection, said mixture of principally monounsaturated lone chain alcohols having the structure:

$$CH_3(CH_2)_m CH=CH(CH_2)_n CH_2OH$$

wherein:
m and n are each independently 5 to 13,
said alcohol comprise 14 to 24 carbon atoms, and
the carbon-carbon double bonds are cis or trans, and b) applying the formulation produced in step (a) to the epidermis of said subject.

6. The method of claim 5 wherein the herpes virus infection is caused by herpes simplex virus-1 (herpes labialis).

7. The method of claim 6 wherein the formulation produced in step (a) is applied to facial area irritations caused by the virus.

8. The method of claim 5 wherein the herpes virus infection is caused by herpes simplex virus-2 (herpes genitalis).

9. The method of claim 8 wherein the formulation produced in step (a) is applied to genital area irritations caused by the virus.

10. The method of claim 5 wherein the herpes virus infection is caused by varicella zoster virus (human herpes virus-3).

11. The method of claim 10 wherein the formulation produced in step (a) is applied to lesions associated with chicken pox.

12. The method of claim 10 wherein the formulation produced in step (a) is applied to lesions associated with shingles.

13. The method of claim 1 wherein the formulation produced in step (a) further consists essentially of 0.05 to 5 wt./vol. % of an antioxidant.

14. The method of claim 13 wherein the antioxidant is a tocopherol.

15. The method of claim 1 wherein the formulation produced in step (a) further consists essentially of 0.05 to 5 wt./vol. % of a low molecular weight organic acid.

16. The method of claim 15 wherein the low molecular weight organic acid is salicylic acid.

17. The method of claim 1 wherein the formulation produced in step (a) further consists essentially of both an antioxidant and a low molecular weight organic acid.

18. The method of claim 1 wherein the pharmaceutically active agent ibuprofen.

19. The method of claim 18 wherein the formulation produced in step (a) is employed for the treatment of pain.

20. The method of claim 1 wherein the pharmaceutically active agent is ketoprofen.

21. The method of claim 20 wherein the formulation produced in step (a) is employed for the treatment of pain.

22. The method of claim 1 wherein the formulation produced in step (a) further consists essentially of a sufficient quantity of low molecular weight alcohol solvent(s) to produce a lotion.

23. The method of claim 22 wherein the low molecular weight alcohol solvent is ethyl alcohol or isopropyl alcohol.

24. A method for transdermal delivery of a pharmaceutically active agent to a subject in need thereof, said method comprising applying to the epidermis of said subject a formulation consisting essentially of said agent and a mixture of principally monounsaturated long chain alcohols having the structure:

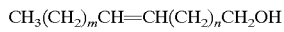

wherein:
m and n are each independently 5 to 13,
said alcohols comprise 14 to 24 carbon atoms, and
the carbon-carbon double bonds are cis or trans.

25. The method of claim 5 wherein the mixture of principally monounsaturated long chain alcohols is produced from joioba oil.

26. The method of claim 5 wherein the mixture of principally monounsaturated long chain alcohols is produced from sperm whale oil.

27. The method of claim 5 wherein the mixture of principally monounsaturated long chain alcohols has a freezing point above three degrees centigrade.

28. A method for the topical treatment of a subject having a herpes virus infection, said method comprising applying to the epidermis of said subject a formulation consisting essentially of a mixture of principally monounsaturated long chain alcohols effective for the topical treatment of herpes virus infection, said mixture of principally monounsaturated long chain alcohols having the structure:

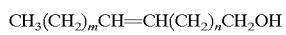

wherein:
m and n are each independently 5 to 13,
said alcohols comprise 14 to 24 carbon atoms, and
the carbon-carbon double bore cia or trans.

29. The method of claim 5 wherein the formulation produced in step (a) further consists essentially of 0.05 to 5 wt./vol. % of an antioxidant.

30. The method of claim 29 wherein the antioxidant is a tocopherol.

31. The method of claim 5, wherein the formulation produced in step (a) further consists essentially of 0.05 to 5 wt./vol. % of a low molecular weight organic acid.

32. The method of claim 31 wherein the low molecular weight organic acid is selected from the group consisting of salicylic acid, acetylsalicylic acid, lactic acid, glycolic acid, pyruvic acid, malic acid, citric acid, furnaric acid and succinic acid.

33. The method of claim 5 wherein the formulation produced in step (a) further consists essentially of both an antioxidant and a low molecular weight organic acid.

34. The method of claim 5 wherein the formulation produced in step (a) further consists essentially of a sufficient quantity of low molecular weight alcohol solvent(s) to produce a lotion.

35. The method of claim 34 wherein the low molecular weight alcohol solvent is ethyl alcohol or isopropyl alcohol.

* * * * *